(12) United States Patent
Buchman, II et al.

(10) Patent No.: US 7,393,354 B2
(45) Date of Patent: Jul. 1, 2008

(54) ELECTROSURGICAL PENCIL WITH DRAG SENSING CAPABILITY

(75) Inventors: Thomas L. Buchman, II, Olathe, KS (US); Ronald J. Podhajsky, Boulder, CO (US); Arlan J. Reschke, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 309 days.

(21) Appl. No.: 10/521,901

(22) PCT Filed: Jul. 23, 2003

(86) PCT No.: PCT/US03/22900

§ 371 (c)(1),
(2), (4) Date: Oct. 5, 2005

(87) PCT Pub. No.: WO2004/010883

PCT Pub. Date: Feb. 5, 2004

(65) Prior Publication Data

US 2006/0058783 A1 Mar. 16, 2006

Related U.S. Application Data

(60) Provisional application No. 60/398,620, filed on Jul. 25, 2002, provisional application No. 60/413,410, filed on Sep. 25, 2002.

(51) Int. Cl.
*A61B 18/14* (2006.01)

(52) U.S. Cl. .............................. 606/42; 606/38; 606/45; 606/49

(58) Field of Classification Search .................. 606/42, 606/45
See application file for complete search history.

(56) References Cited

U.S. PATENT DOCUMENTS

| 2,031,682 | A | 2/1936 | Fred rick et al. |
| 2,102,270 | A | 12/1937 | Hyams |

(Continued)

FOREIGN PATENT DOCUMENTS

| DE | 24 29 021 A1 | 1/1976 |

(Continued)

OTHER PUBLICATIONS

European Search Report from Application EP 07009028 dated Jul. 16, 2007.

(Continued)

*Primary Examiner*—Lee S Cohen

(57) ABSTRACT

An electrosurgical pencil (100) configured and adapted to support an electrocautery blade (116). A strain gauge (130) is affixed to the proximal, end of the electrocautery blade and measures the displacement of the blade as a result of resistance and drag acting on the blade. The electrosurgical pencil also includes a meter electrically connected to the strain gauge for monitoring either a change in voltage, a change in electrical current or a change in optical wavelength. The amount of blade displacement as measured by the strain gauge is available for display to the surgeon and/or as sensory input for a control circuit in the electrosurgical generator (118) that modulates the generator output waveform. The electrosurgical pencil further includes a control circuit electrically coupled between the electrocautery blade and the electrosurgical generator. The control circuit is configured and adapted to control power supplied to electrocautery blade based on the displacement measured by the strain gauge.

18 Claims, 5 Drawing Sheets

U.S. PATENT DOCUMENTS

| | | |
|---|---|---|
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Jr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III. |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,605 A | 1/1993 | Imonti |
| 5,190,517 A | 3/1993 | Zieve et al. |
| 5,190,541 A | 3/1993 | Abele et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,376,089 A | 12/1994 | Smith |
| 5,380,320 A | 1/1995 | Morris |
| 5,382,247 A | 1/1995 | Cimino et al. |

| | | | | | |
|---|---|---|---|---|---|
| 5,395,363 A | 3/1995 | Billings et al. | 5,938,589 A | 8/1999 | Wako et al. |
| 5,399,823 A | 3/1995 | McCusker | 5,941,887 A | 8/1999 | Steen et al. |
| 5,401,273 A | 3/1995 | Shippert | 5,944,737 A | 8/1999 | Tsonton et al. |
| 5,403,882 A | 4/1995 | Huggins | 5,951,548 A | 9/1999 | DeSisto et al. |
| 5,406,945 A | 4/1995 | Riazzi et al. | 5,951,581 A | 9/1999 | Saadat et al. |
| 5,409,484 A | 4/1995 | Erlich et al. | 5,954,686 A | 9/1999 | Garito et al. |
| 5,413,575 A | 5/1995 | Haenggi | 5,972,007 A | 10/1999 | Sheffield et al. |
| 5,421,829 A | 6/1995 | Olichney et al. | 6,004,318 A | 12/1999 | Garito et al. |
| 5,423,838 A | 6/1995 | Willard | 6,004,333 A | 12/1999 | Sheffield et al. |
| 5,431,645 A | 7/1995 | Smith et al. | 6,004,335 A | 12/1999 | Vaitekunas et al. |
| 5,431,650 A | 7/1995 | Cosmescu | 6,010,499 A | 1/2000 | Cobb |
| 5,451,222 A | 9/1995 | De Maagd et al. | 6,022,347 A | 2/2000 | Lindenmeier et al. |
| 5,460,602 A | 10/1995 | Shapira | 6,045,564 A | 4/2000 | Walen |
| 5,462,522 A | 10/1995 | Sakurai et al. | 6,063,050 A | 5/2000 | Manna et al. |
| 5,468,240 A | 11/1995 | Gentelia et al. | 6,068,603 A | 5/2000 | Suzuki |
| 5,472,442 A | 12/1995 | Klicek | 6,068,627 A | 5/2000 | Orszulak et al. |
| 5,472,443 A | 12/1995 | Cordis et al. | 6,070,444 A | 6/2000 | Lontine et al. |
| 5,484,398 A | 1/1996 | Stoddard | 6,071,281 A | 6/2000 | Burnside et al. |
| 5,484,434 A | 1/1996 | Cartmell et al. | 6,074,386 A | 6/2000 | Goble et al. |
| 5,486,162 A | 1/1996 | Brumbach | 6,074,387 A | 6/2000 | Heim et al. |
| 5,496,314 A | 3/1996 | Eggers | 6,086,544 A | 7/2000 | Hibner et al. |
| 5,498,654 A | 3/1996 | Shimasaki et al. | 6,090,123 A | 7/2000 | Culp et al. |
| D370,731 S | 6/1996 | Corace et al. | 6,099,525 A | 8/2000 | Cosmescu |
| 5,531,722 A | 7/1996 | Van Hale | 6,117,134 A | 9/2000 | Cunningham et al. |
| 5,549,604 A | 8/1996 | Sutcu et al. | 6,139,547 A | 10/2000 | Lontine et al. |
| 5,561,278 A | 10/1996 | Rutten | D433,752 S | 11/2000 | Saravia |
| 5,599,346 A | 2/1997 | Edwards et al. | 6,142,995 A | 11/2000 | Cosmescu |
| 5,601,224 A | 2/1997 | Bishop et al. | 6,146,353 A | 11/2000 | Platt, Jr. |
| 5,609,573 A | 3/1997 | Sandock | 6,149,648 A | 11/2000 | Cosmescu |
| 5,626,575 A | 5/1997 | Crenner | 6,156,035 A | 12/2000 | Songer |
| 5,630,426 A | 5/1997 | Eggers et al. | 6,197,024 B1 | 3/2001 | Sullivan |
| 5,630,812 A | 5/1997 | Ellman et al. | 6,200,311 B1 | 3/2001 | Danek et al. |
| 5,633,578 A | 5/1997 | Eggers et al. | D441,077 S | 4/2001 | Garito et al. |
| 5,634,912 A | 6/1997 | Injev | 6,213,999 B1 | 4/2001 | Platt, Jr. et al. |
| 5,634,935 A | 6/1997 | Taheri | 6,214,003 B1 | 4/2001 | Morgan et al. |
| 5,643,256 A | 7/1997 | Urueta | 6,238,388 B1 | 5/2001 | Ellman et al. |
| D384,148 S | 9/1997 | Monson | 6,241,723 B1 | 6/2001 | Heim et al. |
| 5,669,907 A | 9/1997 | Platt, Jr. et al. | 6,241,753 B1 | 6/2001 | Knowlton |
| 5,674,219 A | 10/1997 | Monson et al. | 6,249,706 B1 | 6/2001 | Sobota et al. |
| 5,693,044 A | 12/1997 | Cosmescu | 6,251,110 B1 | 6/2001 | Wampler |
| 5,693,050 A | 12/1997 | Speiser | 6,257,241 B1 | 7/2001 | Wampler |
| 5,693,052 A | 12/1997 | Weaver | 6,258,088 B1 | 7/2001 | Tzonev et al. |
| 5,697,926 A | 12/1997 | Weaver | 6,273,862 B1 | 8/2001 | Privitera et al. |
| 5,702,360 A | 12/1997 | Dieras et al. | 6,277,083 B1 | 8/2001 | Eggers et al. |
| 5,702,387 A | 12/1997 | Arts et al. | 6,287,305 B1 | 9/2001 | Heim et al. |
| 5,712,543 A | 1/1998 | Sjostrom | 6,287,344 B1 | 9/2001 | Wampler et al. |
| 5,713,895 A | 2/1998 | Lontine et al. | 6,312,441 B1 | 11/2001 | Deng |
| 5,720,745 A | 2/1998 | Farin et al. | 6,325,799 B1 | 12/2001 | Goble |
| D393,067 S | 3/1998 | Geary et al. | D453,222 S | 1/2002 | Garito et al. |
| 5,749,869 A | 5/1998 | Lindenmeier et al. | D453,833 S | 2/2002 | Hess |
| 5,765,418 A | 6/1998 | Rosenberg | 6,350,276 B1 | 2/2002 | Knowlton |
| 5,776,092 A | 7/1998 | Farin et al. | 6,352,544 B1 | 3/2002 | Spitz |
| 5,788,688 A | 8/1998 | Bauer et al. | 6,355,034 B2 | 3/2002 | Cosmescu |
| 5,797,907 A | 8/1998 | Clement | 6,358,281 B1 | 3/2002 | Berrang et al. |
| 5,800,431 A | 9/1998 | Brown | 6,361,532 B1 | 3/2002 | Burek |
| 5,836,897 A | 11/1998 | Sakurai et al. | D457,955 S | 5/2002 | Bilitz |
| 5,836,909 A | 11/1998 | Cosmescu | 6,395,001 B1 | 5/2002 | Ellman et al. |
| 5,836,944 A | 11/1998 | Cosmescu | 6,402,741 B1 | 6/2002 | Keppel et al. |
| D402,030 S | 12/1998 | Roberts et al. | 6,402,742 B1 | 6/2002 | Blewett et al. |
| D402,031 S | 12/1998 | Roberts et al. | 6,402,743 B1 | 6/2002 | Orszulak et al. |
| 5,843,109 A | 12/1998 | Mehta et al. | 6,402,748 B1 | 6/2002 | Schoenman et al. |
| 5,846,236 A | 12/1998 | Lindenmeier et al. | 6,409,725 B1 | 6/2002 | Khandkar et al. |
| 5,859,527 A | 1/1999 | Cook | 6,413,255 B1 | 7/2002 | Stern |
| 5,868,768 A | 2/1999 | Wicherski et al. | 6,416,491 B1 | 7/2002 | Edwards et al. |
| 5,876,400 A | 3/1999 | Songer | 6,416,509 B1 | 7/2002 | Goble et al. |
| 5,879,347 A | 3/1999 | Saadat | 6,425,912 B1 | 7/2002 | Knowlton |
| 5,888,200 A | 3/1999 | Walen | 6,458,122 B1 | 10/2002 | Pozzato |
| 5,893,848 A | 4/1999 | Negus et al. | 6,458,125 B1 | 10/2002 | Cosmescu |
| 5,893,849 A | 4/1999 | Weaver | 6,461,352 B2 | 10/2002 | Morgan et al. |
| 5,893,862 A | 4/1999 | Pratt et al. | 6,464,702 B2 | 10/2002 | Schulze et al. |
| 5,913,864 A | 6/1999 | Garito et al. | 6,471,659 B2 | 10/2002 | Eggers et al. |
| 5,919,219 A | 7/1999 | Knowlton | 6,494,882 B1 * | 12/2002 | Lebouitz et al. ............... 606/45 |
| 5,928,159 A | 7/1999 | Eggers et al. | 6,500,169 B1 | 12/2002 | Deng |

| | | | | | |
|---|---|---|---|---|---|
| 6,511,479 B2 | 1/2003 | Gentelia et al. | 2003/0199866 A1 | 10/2003 | Stern et al. |
| 6,526,320 B2 | 2/2003 | Mitchell | 2003/0199869 A1 | 10/2003 | Johnson et al. |
| 6,551,313 B1 | 4/2003 | Levin | 2003/0212393 A1 | 11/2003 | Knowlton et al. |
| 6,558,383 B2 | 5/2003 | Cunningham et al. | 2003/0212397 A1 | 11/2003 | Avrahami et al. |
| 6,585,664 B2 | 7/2003 | Burdorff et al. | 2003/0216728 A1 | 11/2003 | Stern et al. |
| 6,589,239 B2 | 7/2003 | Khandkar et al. | 2003/0220635 A1 | 11/2003 | Knowlton et al. |
| 6,610,054 B1 | 8/2003 | Edwards et al. | 2003/0220638 A1 | 11/2003 | Metzger |
| 6,610,057 B1 | 8/2003 | Ellman et al. | 2003/0225401 A1 | 12/2003 | Eggers et al. |
| 6,616,658 B2 | 9/2003 | Ineson | 2003/0229341 A1 | 12/2003 | Albrecht et al. |
| 6,618,626 B2 | 9/2003 | West, Jr. et al. | 2003/0229343 A1 | 12/2003 | Albrecht et al. |
| 6,620,161 B2 | 9/2003 | Schulze et al. | 2004/0000316 A1 | 1/2004 | Knowlton et al. |
| 6,632,193 B1 | 10/2003 | Davison et al. | 2004/0002704 A1 | 1/2004 | Knowlton et al. |
| 6,652,514 B2 | 11/2003 | Ellman et al. | 2004/0002705 A1 | 1/2004 | Knowlton et al. |
| 6,662,053 B2 | 12/2003 | Borkan | 2004/0010246 A1 | 1/2004 | Takahashi |
| 6,669,691 B1 | 12/2003 | Taimisto | 2004/0015160 A1 | 1/2004 | Lovewell |
| 6,685,701 B2 | 2/2004 | Orszulak et al. | 2004/0015161 A1 | 1/2004 | Lovewell |
| 6,685,704 B2 | 2/2004 | Greep | 2004/0015162 A1 | 1/2004 | McGaffigan |
| 6,702,812 B2 | 3/2004 | Cosmescu | 2004/0015216 A1 | 1/2004 | DeSisto |
| 6,712,813 B2 | 3/2004 | Ellman et al. | 2004/0024395 A1 | 2/2004 | Ellman et al. |
| 6,740,079 B1 | 5/2004 | Eggers et al. | 2004/0024396 A1 | 2/2004 | Eggers |
| 6,747,218 B2 | 6/2004 | Huseman et al. | 2004/0030328 A1 | 2/2004 | Eggers et al. |
| D493,530 S | 7/2004 | Reschke | 2004/0030330 A1 | 2/2004 | Brassell et al. |
| D493,888 S | 8/2004 | Reschke | 2004/0030332 A1 | 2/2004 | Knowlton et al. |
| D494,270 S | 8/2004 | Reschke | 2004/0034346 A1 | 2/2004 | Stern et al. |
| D495,051 S | 8/2004 | Reschke | 2004/0054370 A1 | 3/2004 | Given |
| D495,052 S | 8/2004 | Reschke | 2004/0092927 A1 | 5/2004 | Podhajsky et al. |
| 6,794,929 B2 | 9/2004 | Pelly | 2004/0111087 A1 | 6/2004 | Stern et al. |
| 6,830,569 B2 | 12/2004 | Thompson et al. | 2004/0124964 A1 | 7/2004 | Yulun et al. |
| 6,840,948 B2 | 1/2005 | Albrecht et al. | 2004/0127889 A1 | 7/2004 | Zhang et al. |
| 6,855,140 B2 | 2/2005 | Albrecht et al. | 2004/0143677 A1 | 7/2004 | Pavel |
| 6,902,536 B2 | 6/2005 | Manna et al. | 2004/0147909 A1 | 7/2004 | Johnston et al. |
| 6,905,496 B1 | 6/2005 | Ellman et al. | 2004/0162553 A1 | 8/2004 | Peng et al. |
| 6,923,804 B2 | 8/2005 | Eggers et al. | 2004/0167512 A1 | 8/2004 | Stoddard et al. |
| 6,923,809 B2 | 8/2005 | Eggers et al. | 2004/0172011 A1 | 9/2004 | Yulun et al. |
| 6,939,347 B2 | 9/2005 | Thompson | 2004/0172015 A1 | 9/2004 | Novak |
| 6,955,674 B2 | 10/2005 | Eick et al. | 2004/0172016 A1 | 9/2004 | Bek et al. |
| D515,412 S | 2/2006 | Waaler et al. | 2004/0181140 A1 | 9/2004 | Falwell et al. |
| D521,641 S | 5/2006 | Reschke et al. | 2004/0230262 A1 | 11/2004 | Sartor et al. |
| D535,396 S | 1/2007 | Reschke et al. | 2004/0236323 A1 | 11/2004 | Schoenman et al. |
| 2001/0047183 A1 | 11/2001 | Privitera et al. | 2004/0243120 A1 | 12/2004 | Orszulak et al. |
| 2001/0049524 A1 | 12/2001 | Morgan et al. | 2004/0267252 A1 | 12/2004 | Washington et al. |
| 2002/0019596 A1 | 2/2002 | Eggers et al. | 2004/0267254 A1 | 12/2004 | Manzo et al. |
| 2002/0019631 A1 | 2/2002 | Kidder et al. | 2004/0267297 A1 | 12/2004 | Malackowski |
| 2002/0022838 A1 | 2/2002 | Cunningham et al. | 2005/0033286 A1 | 2/2005 | Eggers et al. |
| 2002/0026145 A1 | 2/2002 | Bagaoisan et al. | 2005/0059858 A1 | 3/2005 | Frith et al. |
| 2002/0035364 A1 | 3/2002 | Schoenman et al. | 2005/0059967 A1 | 3/2005 | Breazeale, Jr. et al. |
| 2002/0049427 A1 | 4/2002 | Wiener et al. | 2005/0065510 A1 | 3/2005 | Carmel et al. |
| 2002/0058958 A1 | 5/2002 | Walen | 2005/0070891 A1 | 3/2005 | DeSisto |
| 2002/0087079 A1 | 7/2002 | Culp et al. | 2005/0085804 A1 | 4/2005 | McGaffigan |
| 2002/0095199 A1 | 7/2002 | West, Jr. et al. | 2005/0096645 A1 | 5/2005 | Wellman et al. |
| 2002/0103485 A1 | 8/2002 | Melnyk et al. | 2005/0096646 A1 | 5/2005 | Wellman et al. |
| 2002/0111622 A1 | 8/2002 | Khandkar et al. | 2005/0096681 A1 | 5/2005 | Kai et al. |
| 2002/0133148 A1 | 9/2002 | Daniel et al. | 2005/0107782 A1 | 5/2005 | Reschke |
| 2002/0151886 A1 | 10/2002 | Wood | 2005/0113817 A1 | 5/2005 | Isaacson et al. |
| 2002/0151887 A1 | 10/2002 | Stern et al. | 2005/0113818 A1 | 5/2005 | Sartor et al. |
| 2002/0156471 A1 | 10/2002 | Stern et al. | 2005/0113823 A1 | 5/2005 | Reschke et al. |
| 2002/0173776 A1 | 11/2002 | Batchelor et al. | 2005/0113824 A1 | 5/2005 | Sartor et al. |
| 2002/0198519 A1 | 12/2002 | Qin et al. | 2005/0113825 A1 | 5/2005 | Cosmescu |
| 2003/0004508 A1 | 1/2003 | Morgan et al. | 2005/0149001 A1 | 7/2005 | Akinobu et al. |
| 2003/0014043 A1 | 1/2003 | Henry et al. | 2005/0154385 A1 | 7/2005 | Heim et al. |
| 2003/0032950 A1 | 2/2003 | Altshuler et al. | 2006/0041257 A1 | 2/2006 | Sartor et al. |
| 2003/0050633 A1 | 3/2003 | Ellman et al. | 2006/0058783 A1 | 3/2006 | Buchman |
| 2003/0055421 A1 | 3/2003 | West et al. | 2006/0178667 A1 | 8/2006 | Sartor et al. |
| 2003/0065321 A1 | 4/2003 | Carmel et al. | 2007/0049926 A1 | 3/2007 | Sartor |
| 2003/0078572 A1 | 4/2003 | Pearson et al. | 2007/0093810 A1 | 4/2007 | Sartor |
| 2003/0083655 A1 | 5/2003 | Van Wyk | | | |
| 2003/0088247 A1 | 5/2003 | Ineson | | FOREIGN PATENT DOCUMENTS | |
| 2003/0109864 A1 | 6/2003 | Greep et al. | | | |
| 2003/0109865 A1 | 6/2003 | Greep et al. | DE | 23 60 481 A1 | 6/1976 |
| 2003/0130663 A1 | 7/2003 | Walen | DE | 30 45 996 | 7/1982 |
| 2003/0144680 A1 | 7/2003 | Kellogg et al. | EP | 0 186 369 A | 7/1986 |
| 2003/0163125 A1 | 8/2003 | Greep | EP | 1050277 | 11/2000 |
| 2003/0199856 A1 | 10/2003 | Hill et al. | EP | 1050279 | 11/2000 |

| | | |
|---|---|---|
| EP | 1082945 | 3/2001 |
| EP | 1293171 | 3/2003 |
| EP | 1645234 | 4/2006 |
| EP | 1656900 | 5/2006 |
| FR | 2235669 | 1/1975 |
| WO | WO94/20032 | 9/1994 |
| WO | WO 96/39086 | 12/1996 |
| WO | WO 98/43264 | 10/1998 |
| WO | WO01/64122 | 9/2001 |
| WO | WO 2002/47568 A1 | 6/2002 |
| WO | WO 2004/010883 A1 | 2/2004 |
| WO | WO 2004/045436 | 6/2004 |
| WO | WO 2004/073753 A2 | 9/2004 |
| WO | WO 2005/060849 A1 | 7/2005 |

OTHER PUBLICATIONS

International Search Report from EP 06 01 4431 dated Oct. 31, 2006.
ISR from EP 05019882.9 dated Feb. 16, 2006.
ISR from EP 05021777.7 dated Feb. 23, 2006.
Jaime M. Vasquez, et al.; Surgical Technology International VII; *Techniques of Treatment of Peritoneal Endometriosis: The Cavitational Ultrasonic Surgical Aspirator;*.
International Search Report from PCT/US03/37111.
International Search Report from PCT/US04/04685.
International Search Report from EP/0401/5980.
International Search Report from PCT/US03/22900.
Interantional Search Report EP 06 005 540.7 dated Sep. 24, 2007.

* cited by examiner

ELECTROSURGICAL PENCIL WITH DRAG SENSING CAPABILITY

CROSS-REFERENCE TO RELATED APPLICATION

The present application claims priority of U.S. Provisional Patent Application Ser. No. 60/398,620 filed Jul. 25, 2002 and U.S. Provisional Patent Application Ser. No. 60/413,410 filed Sep. 25, 2002, the entire contents of each of which are incorporated herein by reference.

BACKGROUND

1. Technical Field

The present invention relates generally to an electrosurgical instrument and, more particularly to an electrosurgical pencil having drag sensing capabilities.

2. Background of Related Art

Electrosurgical instruments have become widely used by surgeons in recent years. Accordingly, a need has developed for equipment that is easy to handle and operate, reliable and safe. By and large, most electrosurgical instruments typically include a hand-held instrument, or pencil, which transfers radio-frequency (RF) electrical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical fulguration.

In particular, electrosurgical fulguration comprises the application of electric spark to biological tissue, for example, human flesh or the tissue of internal organs, without significant cutting. The spark is produced by bursts of radio-frequency electrical energy generated from an appropriate electrosurgical generator. Generally, fulguration is used to dehydrate, shrink, necrose or char the tissue. As a result, the instrument is primarily used to stop bleeding and oozing. These operations are generically embraced by the term "Coagulation". Meanwhile, electrosurgical cutting includes the use of the applied electric spark to tissue which produces a cutting effect. Electrosurgical searing includes utilizing both electrosurgical energy and pressure to melt the tissue collagen into a fused mass.

As used herein the term "electrosurgical pencil" is intended to include instruments which have a handpiece which is attached to an active electrode and are used to coagulate, cut and/or sear tissue. The pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the pencil is connected to a suitable electrosurgical source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

When using electrosurgical instruments in an operation, the active electrode may be rendered less efficient if the tissue distorts or encounters inconsistencies in the tissue. These instances are sensed as a change in the tension required to pass the electrode through the tissue (i.e., "drag").

Also, when using electrosurgical instruments in an operation, the tissue tends to char during the surgical procedure and adhere to the active electrode. When the active electrode is an electrosurgical blade, the charred tissue can in some instances effect the overall performance of the electrosurgical blade. Performance degradation of the blade may reduce the effectiveness of the instrument during the operation. For example, a build up of charred tissue on the active electrode may effect cutting efficiency of the blade. As a result, the surgeon may find it necessary to increase the electrical current to the electrosurgical blade in order to compensate for the degradation of the cutting blade. This raises the possibility that the tissue will be more easily and rapidly charred when contacting the tissue.

Another concern resulting from the build up of charred tissue on the active electrode is that the charred tissue can fracture and contaminate the surgical site which may delay the overall healing process. The build up of charred tissue on the active electrode may also increase drag (i.e., the amount of resistance the body tissue exhibits during cutting). Drag may distort the tissue and consequently alter anatomical relationships which can effect proper suturing, possibly delay healing, and result in more visible scarring.

Accordingly, the need exists for an electrosurgical pencil which includes drag sensing capabilities to readily alert the operator when the drag force acting on the electrosurgical blade has surpassed a predetermined threshhold level and/or the electrosurgical blade has been displaced beyond a predetermined acceptable level.

SUMMARY

An electrosurgical pencil being configured and adapted to provide an operator with the ability to monitor the degree of drag taking place at the cutting tip of the electrosurgical pencil, as the cutting tip is advanced through body tissue, is disclosed. The electrosurgical pencil includes an elongated housing having a blade receptacle provided at a distal end thereof, an electrocautery blade supported within the blade receptacle, wherein the blade has a distal end extending distally from the housing and a proximal end extending into the housing, an activation button electrically coupled to the blade and a strain gauge affixed to the electrocautery blade for measuring a displacement of the blade. Preferably, the strain gauge is either a wire, a foil, a semiconductor material or an optical strain transducer.

In a preferred embodiment, the strain gauge includes a temperature compensator resistor electrically coupled to the strain gauge or a temperature compensated transducer. The compensator resistor being configured and adapted to compensate for displacement variations due to changes in temperature.

In a further preferred embodiment, the activation button is supported on the housing. In another preferred embodiment, the strain gauge is mechanically coupled to a proximal end of the electrocautery blade.

It is contemplated that the strain gauge mounted in the electrosurgical pencil is connected to an appropriate signal conditioner that monitors a change in voltage, a change in electrical current and/or a change in optical wavelength.

It is contemplated that the electrosurgical pencil provide an indication of the mechanical resistance of the blade passing through tissue in terms of strain gauge signal amplitude. This strain signal output provides sensor feedback in a control system that controls the wave form output of the electrosurgical generator.

It is further contemplated that the electrosurgical pencil preferably include means for producing a signal when the strain gauge measures a displacement of the blade which satisfies a predetermined level and, more preferably a feedback system which produces an audible and/or a visible signal when the predetermined level is met.

In an alternative embodiment, electrosurgical instrument includes a control circuit electrically coupled between the electrocautery blade and the electrosurgical generator. The control circuit is configured and adapted to control power supplied to electrocautery blade based on the displacement measured by the strain gauge. Preferably, the control circuit is configured and adapted to increase the power supplied to the electrocautery blade when the displacement of the electrocautery blade, measured by the strain gauge, is greater than a preset value and decreases the power supplied to the electrocautery blade when the displacement of the electrocautery blade, measured by the strain gauge, is less than a preset value.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
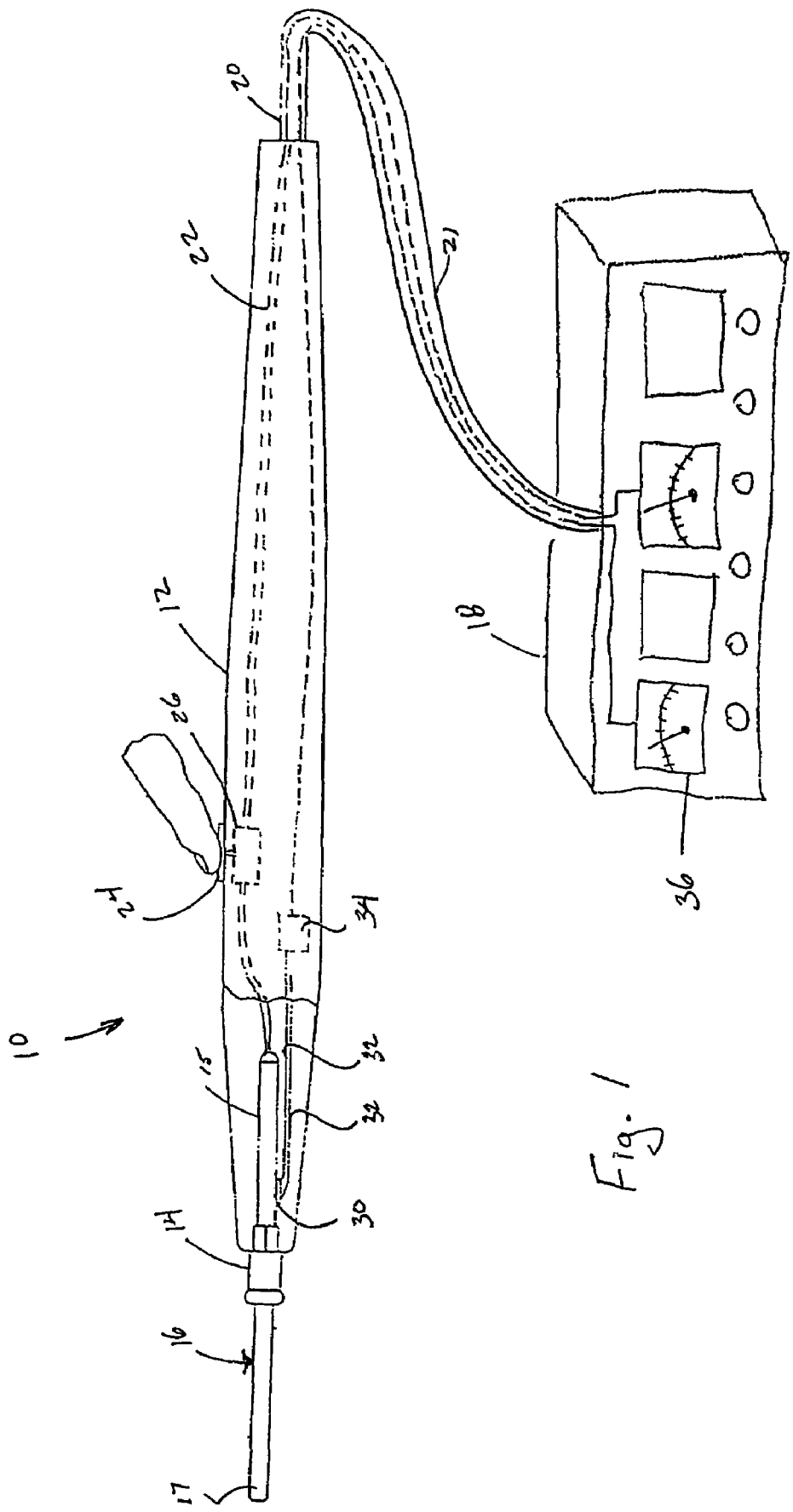
FIG. 1 is a partially broken away side elevational view of an embodiment of an electrosurgical pencil in accordance with the present disclosure.

Preferred embodiments of the presently disclosed electrosurgical pencil will now be described in detail with reference to the drawing figures wherein like reference numerals identify similar or identical elements. As used herein, the term "distal" refers to that portion which is further from the user while the term "proximal" refers to that portion which is closer to the user.

FIG. 1 sets forth a partially broken away side elevational view of an electrosurgical pencil constructed in accordance with the present invention and generally referenced by numeral 10. While the following description will be directed towards an electrosurgical pencil it is envisioned that the inventive features of the present disclosure can be applied to any electrosurgical type instrument Electrosurgical pencil 10 includes an elongated housing 12 configured and adapted to support a blade receptacle 14 at a distal end thereof which, in turn, receives a replaceable electrocautery blade 16 therethrough. A distal portion 17 of blade 16 extends distally from receptacle 14 and a proximal portion 15 of blade 16 is retained within the distal end of housing 12. It is contemplated that electrocautery blade 16 may be fabricated from a conductive type material, i.e., stainless steel or coated with an electrically conductive material.

As shown, electrosurgical pencil 10 is coupled to a conventional electrosurgical generator 18 via connecting wire 20. Connecting wire 20 includes a current wire 22 which electrically interconnects electrosurgical generator 18 and the proximal end of blade 16 and a coating 21 which electrically insulates and encapsulates current wire 22 to protect the operator from stray electrical currents. By way of example only, electrosurgical generator 18 may be any one the following, or equivalents thereof: the "FORCE FX", "FORCE 2" or "FORCE 4" generators manufactured by Valleylab, Inc of Boulder, Co. Ideally, the electrosurgical generator can be preset to selectively provide an appropriate first predetermined RF signal (e.g., 1 to 300 watts) for tissue cutting and an appropriate second predetermined RF signal (e.g., 1 to 120 watts) for tissue coagulation.

Electrosurgical pencil 10 further includes an activation button 24 supported on an outer surface of housing 12. Activation button 24 is operable to control a depressible switch 26 which is used to control the RF electrical energy supplied to blade 16. It is contemplated that electrosurgical pencil 10 further includes an electrical control circuit (not shown) which is electrically coupled between current wire 22 and activation button 24. In one embodiment the control circuit includes conventional on/off connection capabilities as well as high/low power capabilities utilizing a conventional resistive matrix. It will be apparent to those skilled in the art that virtually any control circuit may be utilized which regulates/monitors the electrical energy passing through current wire 22 between depressible switch 26 and blade receptacle 14.

In accordance with the present invention, electrosurgical pencil 10 further includes a strain gauge 30 (i.e., a device used to measure mechanical displacement/deflection) mounted to the surface of the proximal end 15 of blade 16. Strain gauge 30 includes a pair of signal wires 32 electrically or a pair of optical fibers 33 (see FIG. 2) optically interconnecting strain gauge 30 to electrosurgical generator 18. Signal wires 32 and/or optical fibers 33 extend from strain gauge 30, through housing 12 and connecting wire 20, to a meter 36 provided on generator 18. In operation, strain gauge 30 converts small mechanical displacements of blade 16 to electrical or optical signals. The electrical signals reflect the resistance of the meter during displacement, i.e., when a metal is stretched its resistance increases or when an optical transducer is stretched its optical properties change. The measurement of the change in the resistance of the metal in the strain gauge enables the user to readily determine the degree of displacement which corresponds to the change in blade 16. Many different electrical devices may be employed to measure the electrical signal generated from the strain gauge, e.g., voltage meter, amp meter, etc.

It is contemplated that strain gauge 30 be made of wire, foil or semiconductor material. Wire and foil strain gauges are typically constructed by cementing a high-resistance metal to a backing of paper or epoxy, which is then cemented to the structural element (i.e., the proximal end 15 of blade 16). It is contemplated that in order to obtain a higher resistance, the wire or foil making up the strain gauge is often folded in a zig-zag pattern on the backing. As is known in the art, many of the wires and foils which have desirable characteristics as strain gauge materials are also sensitive to changes in temperature. In other words, changes in temperature will alter the resistance of the wire. Thus, in the present instance, wherein changes in temperature in blade 16 are likely, it is contemplated that strain gauge 30 be provided with a compensator resistor 34, placed in close proximity to the strain gauge. Preferably, resistor 34 is configured to compensate for the changes in temperature experienced by blade 16 which are measured by strain gauge 30. It is further contemplated that a semiconductor strain gauge made up of piezoresistive material, usually silicone, be used. In operation, when pressure (i.e., resistance due to drag) is applied to the underlying substrate (i.e., blade 16), the resistance of the metal making up the strain gauge is altered and typically a change in the output voltage and/or electrical current can be monitored. Alternatively, strain gauge 30 could be an optical transducer.

Figure 2:
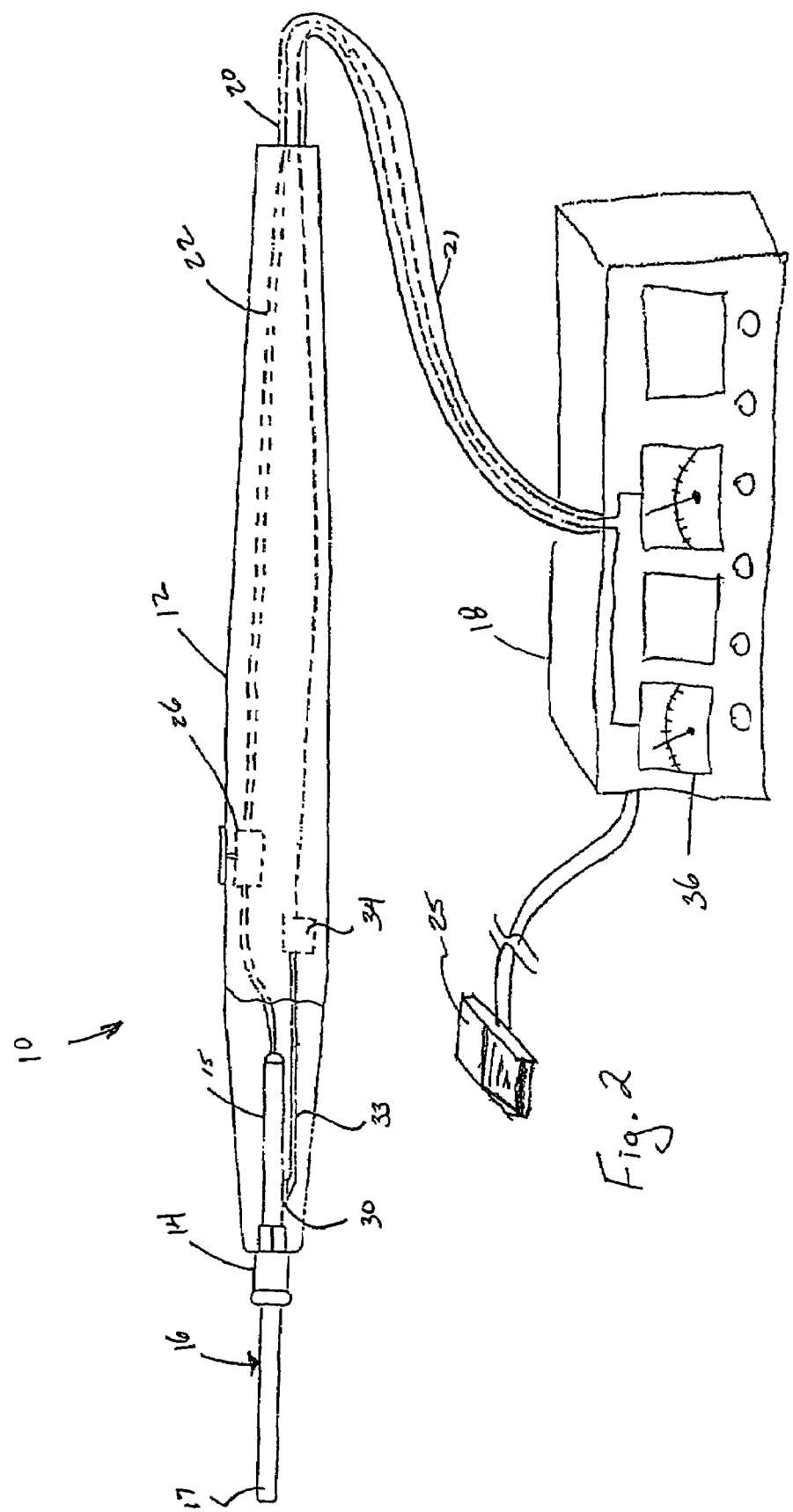
FIG. 2 is a partially broken away side elevational view of another embodiment of an electrosurgical pencil in accordance with the present disclosure.

As seen in particular in FIG. 2, strain gauge 30 of electrosurgical pencil 10 includes a pair of optical fibers 33 optically interconnecting strain gauge 30 to electrosurgical generator 18. Optical fibers 33 extend from strain gauge 30, through housing 12 and connecting wire 20, to a meter 36 provided on generator 18. It is further contemplated, that instead of a finger actuated activation button 24, that electrosurgical pencil 10 include a foot switch 25 electrically coupled thereto via electrosurgical generator 18 for controlling the RF electrical energy supplied to blade 16.

As used in the present invention, as the drag acting against the distal end 17 of blade 16 increases, due to the pressure applied by the operator and/or the build up of charred tissue on blade 16, the deflection and/or displacement of the proximal end 15 of blade 16 will also increase. The displacement of the proximal end 15 of blade 16 is measured by strain gauge 30 which, in turn, converts this displacement into an electrical or optical signal which can be monitored on generator 18. Accordingly, as the operator uses pencil 10 to cut or coagulate, the operator continually monitors meter 36 for any significant changes which surpass a predetermined threshold level. These changes alert the operator that either: 1) the advancement of blade 16 through the tissue site is too fast which may result in the tissue becoming distorted; or 2) that the build up of charred tissue on blade 16 is approaching a level at which continued advancement of electrosurgical pencil 10 may cause the tissue to become distorted.

It is contemplated that electrosurgical pencil 10 may be provided with a feedback system, as will be described in greater detail below, connected to the electrosurgical generator. The feedback of the sensed drag would contribute an input to a control circuit in the generator that modulates the generator output waveform. For example, increased drag would indicate the need for increasing the output current to the active electrode.

It is further contemplated that electrosurgical pencil 10 may be provided with an audible or visible (i.e., light) feedback system (not shown) which would indicate to the operator when the drag acting on the distal end of blade 16 is approaching, has equaled or has surpassed the predetermined threshold level. For example, feedback system can include a buzzer and/or light which are set to be activated when the level on meter 36 reaches a certain predetermined number or range level. In this manner, the operator does not have to actively monitor meter 36. Instead, the operator can focus on the target tissue site and be alerted either by the sound of a buzzer, by the flashing of a light, or by both when the resistance acting against the advancement of the distal end of blade 16 has become greater than the predetermined threshold level. Over time, it is envisioned that the operator of electrosurgical pencil 10 will condition himself or herself to tactily recognize when the resistance on the distal end of blade 16 is becoming too great.

Figure 3:
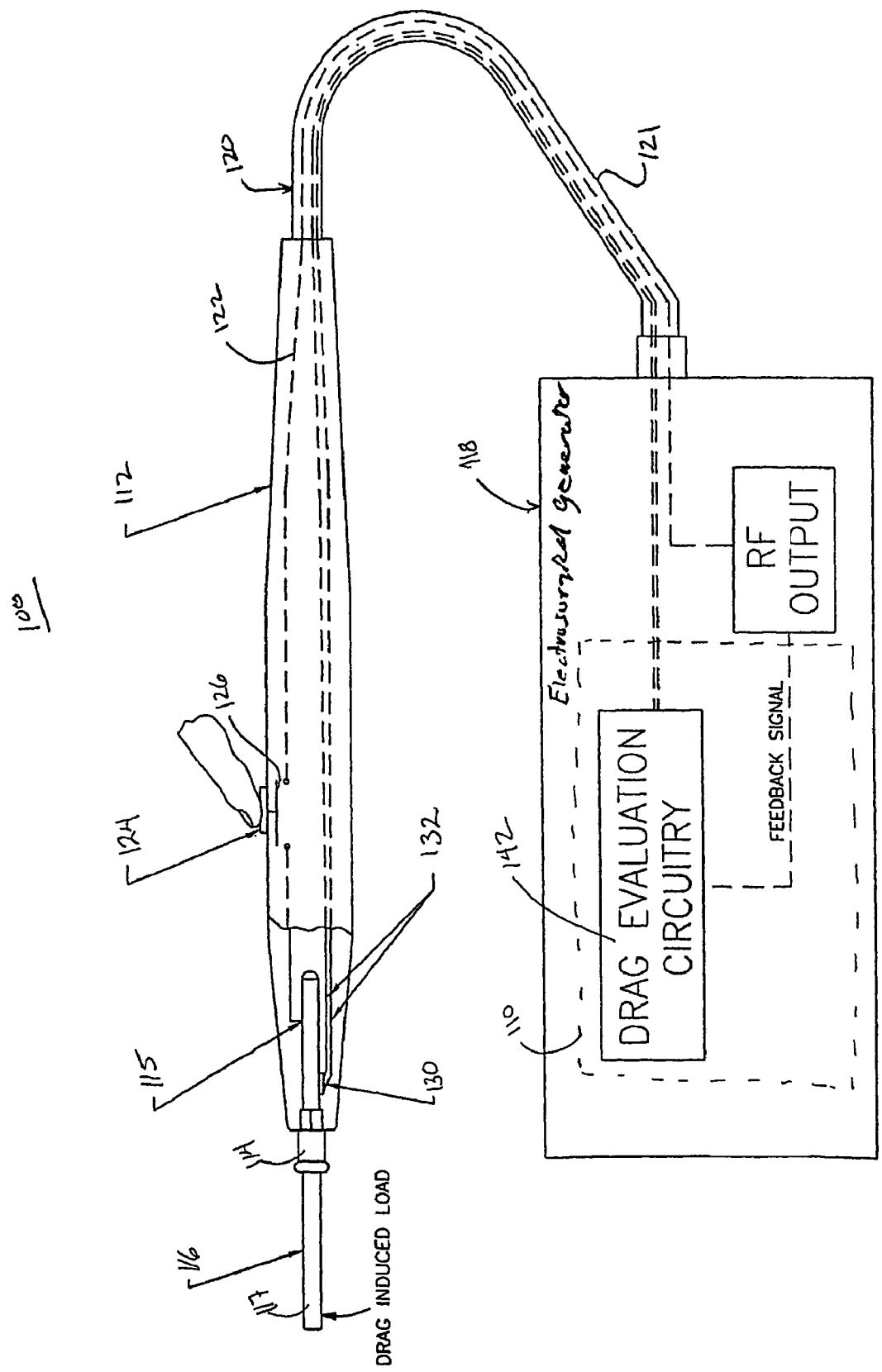
FIG. 3 is a partial broken away side elevational view of yet another embodiment of an electrosurgical pencil in accordance with the present disclosure illustrating a control circuit for automated control of an electrosurgical generator output.
Figure 4:
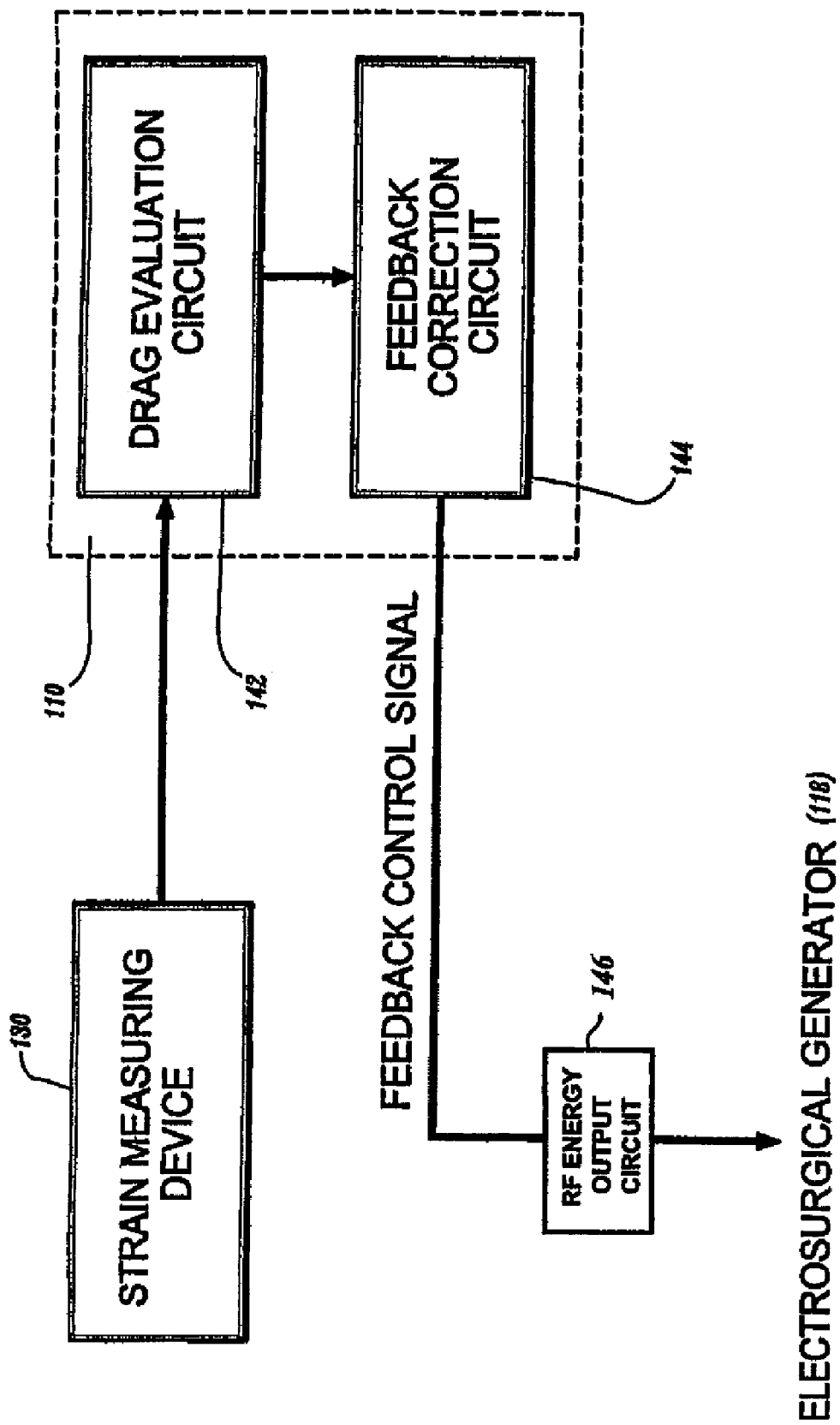
FIG. 4 is a schematic flow chart of the electrosurgical generator used in connection with the electrosurgical pencil of FIG. 3.
Figure 5:
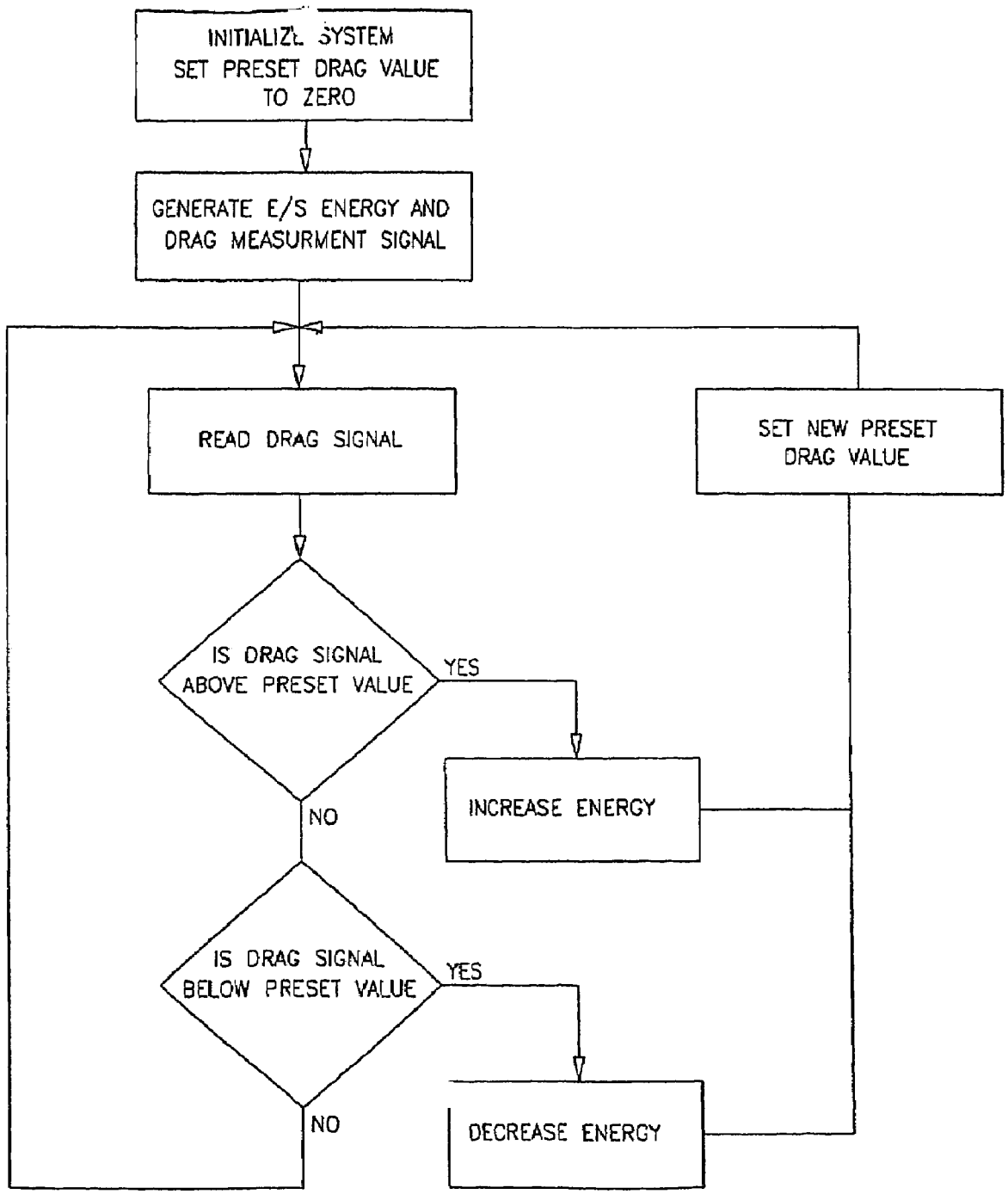
FIG. 5 is a schematic flow chart of a drag evaluation circuit of the control circuit.

Turning now to FIGS. 3-5, an electrosurgical pencil 100 having a control circuit 110 configured and adapted for the automated control of an electrosurgical generator 118 is disclosed. As seen in FIG. 3, electrosurgical pencil 100 includes an elongated housing 112 configured and adapted to support a blade receptacle 114 at a distal end thereof which, in turn, receives a replaceable electrocautery blade 116 therethrough. A distal portion 117 of blade 116 extends distally from receptacle 114 and a proximal portion 115 of blade 116 is retained within the distal end of housing 112.

As shown, electrosurgical pencil 100 is coupled to a conventional electrosurgical generator 118 via connecting wire 120. Connecting wire 120 includes a current wire 122 which electrically interconnects electrosurgical generator 118 and the proximal end of blade 116 and a coating 121 which electrically insulates and encapsulates current wire 122 to protect the operator from stray electrical current Electrosurgical pencil 100 further includes an activation button 124 supported on an outer surface of housing 112. Activation button 124 is operable to control a depressible switch 126 which is used to control the RF electrical energy supplied to blade 116. It is contemplated that electrosurgical pencil 100 further includes an electrical control circuit 110 which is electrically coupled between current wire 122 and activation button 124. In one embodiment, control circuit 110 includes conventional on/off connection capabilities as well as high/low power capabilities utilizing a conventional resistive matrix.

As seen in FIG. 3, electrosurgical pencil 100 further includes a strain gauge 130 mounted to the surface of the proximal end 115 of blade 116. Strain gauge 130 includes a pair of signal wires 132 electrically interconnecting strain gauge 130 to electrosurgical generator 118. Signal wires 132 extend from strain gauge 130, through housing 112 and connecting wire 120, to electrical control circuit 110 of generator 118.

One mode of operation of electrical control circuit 110 is best illustrated with reference to FIG. 4. As seen in FIG. 4, strain measuring device or strain gauge 130 converts a small mechanical displacement of blade 116 to an electrical signal which electrical signal is transmitted through signal wires 132 to a drag evaluation circuit 142 of control circuit 110. It is envisioned that drag evaluation circuit 142 is configured and adapted to receive the electrical signal from strain gauge 130 and evaluate or compare the electrical signal against a preset or know value. Drag evaluation circuit 142 then transmits an evaluation signal to a feedback correction circuit 144 of control circuit 110 which in turn transmits a feedback control signal to an RF energy output circuit 146 of electrosurgical generator 118. RF energy output circuit 146 instructs electrosurgical generator 118 of the change in power, current or voltage to be supplied to blade 116.

Operation of control circuit 110 will now be described in detail with reference to FIG. 5. Electrosurgical pencil 100 and electrosurgical generator 118 are initialized such that strain gauge 130 of blade 116 is calibrated to produce an initial drag value of zero. The surgeon then sets electrosurgical pencil to a desired "drag value" and activates electrosurgical pencil 100 by depressing activation switch 124 thus permitting energy (i.e., electrical current, voltage, etc.) to flow to blade 116. The surgeon then commences the electrosurgical procedure by touching blade 116 to the target surgical site (i.e., body tissue, skin, organ, etc.) at which time blade 116 begins to displace due to the drag sensed thereon. The displacement due to the drag in turn causes strain gauge 130 to produce a drag signal which is transmitted to control circuit 110 of electrosurgical generator 118. Drag evaluation circuit 142 of control circuit 110 receives the measured drag signal and evaluates or compares the measured drag signal against the preset "drag value."

If the measured drag signal is above the preset "drag value", drag evaluation circuit 142 transmits a signal to feedback correction circuit 144 which in turn instructs electrosurgical generator 118 to increase the energy output to blade 116.

In addition, feedback correction circuit 144 resets the "drag value" to the value of the higher measured drag signal. If the measured drag signal is not above the preset "drag value", drag evaluation circuit 142 evaluates to see if the measured drag signal is below the preset "drag value." If the measured drag signal is below the preset "drag value", drag evaluation circuit 142 transmits a signal to feedback correction circuit 144 which in turn instructs electrosurgical generator 118 to decrease the energy output to blade 116. In addition, feedback correction circuit 144 resets the "drag value" to the value of the lower measured drag signal. If the measured drag signal is not below the preset "drag value" the evaluation process repeats from the beginning.

This evaluation process is continually ongoing so long as electrosurgical pencil 100 is activated. Preferably, the evaluation process occurs on the order of 100 times per second. In this manner, the power delivered to blade 116 is constantly monitored and adjusted in order to ensure that minimal trauma to the target site occurs. It is envisioned that the evaluation rate can be adjusted as needed. For example, a higher rate of evaluation may be desired for more delicate target surgical sites while a reduced rate of evaluation may be desired for hardier target sites.

It is envisioned that control circuit 110 can be provided with a cut-off control circuit (not shown). Cut-off control circuit would prevent the power being delivered to blade 116 from exceeding a threshold value in order to prevent electrosurgical pencil 100 from transmitting a damaging amount of energy to the target surgical site.

While the present invention has been particularly shown and described with reference to the preferred embodiments thereof, it will be understood by those skilled in the art that the foregoing and other changes in form and details may be made therein without departing from the spirit and scope of the invention. For example, as discussed above, while the present invention has been described as being used in connection with an electrosurgical pencil, it is envisioned that the present invention can be used in connection with any electrocautery device. Therefore, the above description should not be construed as limiting, but merely as exemplifications of preferred embodiments. Those skilled in the art will envision other modifications within the scope and spirit of the present disclosure.

What is claimed is:

1. An electrosurgical pencil, comprising:
   an elongated housing having a blade receptacle provided at a distal end thereof;
   an electrocautery blade supported within the blade receptacle, the blade having a distal end extending distally from the housing and a proximal end extending into the housing;
   an activation button electrically coupled to the blade;
   a strain gauge affixed to the electrocautery blade for measuring a displacement of the blade, wherein the strain gauge is sensitive to a temperature change associated with the electrocautery blade; and
   a compensator resistor operatively connected to the strain gauge, wherein the compensator resistor is configured to compensate for changes in temperature of the electrocautery blade that effect the strain gauge.

2. An electrosurgical pencil according to claim 1, wherein the activation button is supported on the housing.

3. An electrosurgical pencil according to claim 1, wherein the strain gauge is affixed to a proximal end of the electrocautery blade.

4. An electrosurgical pencil according to claim 1, further comprising: a meter which is at least one of electrically and optically connected to the strain gauge for monitoring at least one of a change in voltage, a change in electrical current and a change in optical wavelength.

5. An electrosurgical pencil according to claim 4, wherein the strain gauge is one of a wire, a foil, a semiconductor material and an optical transducer.

6. An electrosurgical pencil according to claim 5, wherein the compensator resistor is also electrically coupled to a temperature compensated transducer, the compensator resistor being configured and adapted to compensate for displacement variations due to changes in temperature.

7. An electrosurgical pencil according to claim 5, wherein the semiconductor material is a piezoresistive material.

8. An electrosurgical pencil according to claim 1, further comprising: means for producing a signal when the strain gauge measures a displacement of the blade which satisfies a predetermined level.

9. An electrosurgical pencil according to claim 8, wherein the means for producing a signal include a feedback system which produces at least one of an audible and a visible signal.

10. An electrosurgical instrument, comprising:
    a housing;
    an electrocautery blade supported within the housing and extending partially therefrom, the blade adapted to connect to an electrosurgical generator which provides electrosurgical energy to the blade;
    an activation switch coupled to the generator which permits selective activation of the electrocautery blade;
    a strain gauge in communication with the electrocautery blade for measuring a displacement of the electrocautery blade, wherein the strain gauge is sensitive to a temperature change associated with the electrocautery blade; and
    a compensator resistor operatively connected to the strain gauge, wherein the compensator resistor is configured to compensate for changes in temperature of the electrocautery blade that effect the strain gauge.

11. An electrosurgical instrument according to claim 10, further comprising means for monitoring at least one of a voltage, an electrical current and an optical wavelength passing through the strain gauge.

12. An electrosurgical instrument according to claim 10, further comprising means for monitoring at least one of a change in voltage, a change in electrical current and a change in an optical wavelength passing through the strain gauge.

13. An electrosurgical instrument according to claim 10, wherein the strain gauge is one of a wire, a foil, a semiconductor material and an optical transducer.

14. An electrosurgical instrument according to claim 10, further comprising: means for producing a signal when the strain gauge measures a displacement of the blade which satisfies a predetermined level.

15. An electrosurgical instrument according to claim 10, wherein the electrosurgical instrument is an electrosurgical pencil having an elongate housing.

16. An electrosurgical instrument according to claim 10, further comprising: a signal producing device configured and adapted to produce a signal when the strain gauge measures a displacement of the electrocautery blade, the electrocautery blade providing a sensory input to a control circuit of the electrosurgical generator which in turn modifies the generator output waveform.

17. An electrosurgical instrument according to claim 16, wherein the control circuit is electrically coupled between the electrocautery blade and the electrosurgical generator, the control circuit being configured and adapted to control power supplied to electrocautery blade based on the displacement measured by the strain gauge.

18. An electrosurgical instrument according to claim 17, wherein the control circuit increases the power supplied to the electrocautery blade when the displacement of the electrocautery blade measured by the strain gauge is greater than a preset value and decreases the power supplied to the electrocautery blade when the displacement of the electrocautery blade measured by the strain gauge is less than a preset value.

* * * * *